United States Patent [19]

Hoy et al.

[11] Patent Number: 5,489,436
[45] Date of Patent: Feb. 6, 1996

[54] TASTE MASK COATINGS FOR PREPARATION OF CHEWABLE PHARMACEUTICAL TABLETS

[75] Inventors: Michael R. Hoy, Sellersville; Edward J. Roche, Paoli, both of Pa.

[73] Assignee: McNeil-PPC, Inc., Milltown, N.J.

[21] Appl. No.: 166,111

[22] Filed: Dec. 13, 1993

Related U.S. Application Data

[63] Continuation-in-part of Ser. No. 715,949, Jun. 14, 1991, abandoned.

[51] Int. Cl.⁶ ............................................. A61K 9/20
[52] U.S. Cl. .................... 424/441; 424/480; 424/482; 514/960; 514/974
[58] Field of Search ........................ 424/441, 494, 424/497, 461, 462; 514/952, 960, 974

[56] References Cited

U.S. PATENT DOCUMENTS

| | | | |
|---|---|---|---|
| 4,800,087 | 1/1989 | Mehta | 424/497 |
| 4,851,226 | 7/1989 | Julian et al. | 424/441 |

*Primary Examiner*—Edward J. Webman
*Attorney, Agent, or Firm*—Bernard F. Plantz

[57] ABSTRACT

Chewable tablets are made from a coated medicament wherein the coating comprises a mixture of dimethylaminoethyl methacrylate and neutral methacrylic acid ester and a cellulose ester, e.g. cellulose acetate, cellulose acetate butyrate, cellulose triacetate or a combination thereof and optionally polyvinyl pyrrolidone, and a process for making such tablets and a method of providing taste masking and sustained releasing of medicaments utilizing such coatings.

12 Claims, No Drawings

TASTE MASK COATINGS FOR PREPARATION OF CHEWABLE PHARMACEUTICAL TABLETS

This application is a continuation-in-part of application Ser. No. 07/715,949, filed Jun. 14, 1991, abandon which is hereby incorporated by reference.

FIELD OF THE INVENTION

This invention relates to tablets containing means to mask the taste of active ingredients. More particularly, the taste masking of active ingredients is achieved by coating a pharmaceutical active material with a reverse enteric polymer coating system.

BACKGROUND OF THE INVENTION

Orally administered medicaments are given to the patient in many forms, such as liquid solutions, emulsions, or suspensions, or in solid form such as capsules or tablets (as used herein, the term "tablet" means any shaped and compressed solid dosage form, including caplets). Medicaments administered in tablet or capsule form are usually intended to be swallowed whole. Therefore, the often disagreeable taste of the active ingredient need not be taken into account in formulating the medicine, except for the provision of means to prevent the taste from being apparent during the short time that the medicine is in the mouth. Such means may include the provision of an appropriately thin and quickly dissolving coating on the tablet, the use of the gelatin capsule form (the gelatin outer shell of the capsule keeps the active ingredient inside until the capsule has been swallowed), or simply compressing a tablet firmly so that it will not begin to disintegrate during the short time that it is intended to be in the mouth.

Children, older persons, and many other persons have trouble swallowing whole tablets and even capsules. Therefore, in cases where the dosage to be administered cannot be made into a very small tablet or capsule, it is desirable to provide the medicine either in liquid form or in a chewable solid form, in addition to the tablet or capsule that is designed to be swallowed whole. Even where the medicine can be formulated as a liquid, it is desirable also to be able to provide a chewable solid form (i.e. tablets) because of added convenience versus carrying a supply of liquid medicine.

A common problem with chewable tablet forms is the often disagreeable taste of the active ingredient which manifests itself during chewing. In some cases, the taste of the active medicament in a tablet can be overpowered by adding flavoring ingredients to the tablet so that when it is chewed, the taste of the active ingredient is simply overpowered. For instance, this has been done with children's aspirin where the dosage is small enough so that the amount of flavoring agents needed to mask the taste of the medicine is not so great that the tablet becomes unreasonably large. A different approach is taken with a commercially available children's size tablet of acetaminophen (acetyl para-aminophenol or "APAP") wherein the APAP is present in granules that are coated with ethyl cellulose. A significant proportion of the APAP remains shielded by the coating (and therefore does not contribute to taste) while the tablet is in the mouth, despite some breakage of the ethyl cellulose coating during compression of the tablet and some additional breakage of the coating during chewing. The APAP becomes bioavailable via permeation through the coating (although ethyl cellulose is not soluble in aqueous fluids, water does permeate through the coating) and from the granules where the coating is broken.

Examples of taste masked coating systems are disclosed in the following references. U.S. Pat. No. 4,851,226, issued Jul. 25, 1989, discloses chewable medicament tablets wherein granules of active ingredient are directly coated with a blend of cellulose acetate or cellulose acetate butyrate and polyvinylpyrrolidone. Commonly assigned U.S. Pat. No. 5,215,755, issued Jun. 1, 1993, discloses chewable medicament compositions comprising a rotogranulation blend of from about 88 to about 97.5% medicament, about 2 to about 10% polyvinylpyrrolidone (PVP) and about 0.5 to about 2.0% sodium lauryl sulfate (SLS), by weight of the weight of the total composition. In further embodiments a coating of hydroxyethyl cellulose (HEC) or a mixture of hydroxyethyl cellulose and hydroxypropyl methylcellulose (HPMC) is added to these rotogranulated particles. Commonly assigned U.S. Pat. No. 5,075,114, issued Dec. 24, 1991, discloses a chewable medicament comprising a coating for active medicament comprising a polymer blend of cellulose acetate and/or cellulose butyrate and water soluble hydroxypropyl cellulose to provide a taste masked and/or sustained release coating.

The present invention is directed to the discovery of a reverse enteric coating process for active medicaments which can achieve a better balance between taste masking, dissolution and rate of bioavailability than other previously known coating combinations.

SUMMARY OF THE INVENTION

As embodied and fully described herein, the present invention provides a chewable tablet comprising a medicament coated with a taste masking effective amount of a polymer blend of at least 5% by weight of a blend of dimethylaminoethyl methacrylate and neutral methacrylic acid ester (MM/MAE) and a cellulose ester (CE). Preferably the cellulose ester (CE) is at least one of cellulose acetate (CA), cellulose acetate butyrate (CAB) or cellulose triacetate (CTA). In a further embodiment of the invention, the polymer blend additionally comprises polyvinylpyrrolidone (PVP) and/or 2-vinyl pyridine(V)/styrene(S) copolymer in a polymer weight ratio of about 65/35 or 80/20 (V/S).

In preferred embodiments, the medicament coated is selected from the group consisting of acetaminophen (APAP), ibuprofen, ibuprofen sodium, dexibuprofen lysinate, naproxen, naproxen sodium, and other similar NSAID's, psyllium, and the general class of antihistamines (e.g. chlorpheniramine, astemizole) gastrointestinal drugs (e.g. famotidine, loperamide, ranitidine and cimetidine) and decongestants (e.g. pseudoephedrine). The medicament is preferably directly coated or granulated if their physical shape (e.g. irregular) or size (e.g. small) discourages uniform coating. The polymer coating comprises about 2 to 55% by weight of the total weight of the coated medicament composition. The coated particles may then be compressed into tablet form together with excipients and flavoring agents to produce chewable tablets.

The invention also provides a process of coating medicaments and methods of using the coated medicaments to make taste masked and/or sustained release chewable tablets.

DETAILED DESCRIPTION OF THE INVENTION

The invention will now be described specifically in terms of its most preferred embodiments which are the preparation of reverse enteric coated medicaments and chewable tablets comprising the coated medicament. Reference will also be made in detail herein to other preferred embodiments of the compositions, processes and methods of the invention.

Reverse enteric coatings are defined herein as coatings which are not water soluble at non-acidic pH's, e.g., in the mouth, but are soluble in the fluids of the gastrointestinal tract, e.g., in the stomach having lower pH's, i.e., pH 1.0 to about 3.5–4.0. The application of this pH solubility profile to taste masking is possible because of the initial insolubility of the coating in the mouth and subsequent ready release and bioavailability of the medicament in the acid medium of the gut or stomach where the coating is soluble.

In accordance with a preferred embodiment of the invention, the polymer blend utilized comprises both a cellulose ester (CE) and a dimethylaminoethyl ethyl methacrylate and neutral methacrylic acid ester (MM/MAE) component. Separately, the solubility of the CE component is pH independent and the MM/MAE component is pH dependent. Combining the two polymers in various ratios will cause the subsequently formed polymer film coat to be more or less prone to diffusion of solute, porous to solute and/or soluble in solute. The degree of diffusion, porosity and/or solubility of the film coat depends on the ratio of CE:MM/MAE and the physicochemical properties of the drug to be taste masked.

This pH sensitivity is introduced to the polymer blend upon the addition MM/MAE such that at pH's less than 3.5–5.0 the polymer blend film becomes porous due to the formation of polymeric salts which are more soluble than MM/MAE resulting in drug release. Approaching the neutral to weakly alkaline range (pH 5.0–6.0), the MM/MAE, rather than forming soluble polymeric salts, begins to swell and becomes more permeable to water (diffusion). At pH 6–7, as is encountered in the mouth, MM/MAE films are resistant to solubility and are taste proof for approximately 30–60 seconds since it takes at least this long for water to diffuse through the polymer film coat.

From a physicochemical perspective, if the drug of interest is relatively water soluble the relative amount of CE would have to be increased in order to taste mask the drug in the mouth. If the drug of interest is less water soluble, the relative amount of CE would be lower in order to attain the same degree of taste masking seen with the more water soluble drug.

The polymer blend of CE and MM/MAE is also advantageous in enhancing the durability of coated particles when compressed, since MM/MAE used alone is not a highly durable film due to its relatively brittle nature. MM/MAE used alone is likely to be broken during compression and/or during chewing of the tablet, whereas the polymer blend of CE and MM/MAE is more flexible and less likely to be broken.

The coating process is also made easier with the polymer blend of the invention versus use of MM/MAE alone. MM/MAE in the presence of residual solvent can develop tackiness during processing. High tackiness during processing leads to increased particle-particle sticking. Particle agglomeration decreases efficiency of coating leading to erratic drug release profiles from batch to batch. In addition, if tackiness occurs extensively the granulation will ball up into one solid mass and further processing would not be possible. If MM/MAE is used in combination with CE this tackiness is reduced and processing is improved.

In accordance with preferred embodiments of the invention the raw medicament is reverse enteric coated directly. In cases where the raw medicament is of irregular shape or small size, the raw medicaments are first granulated to produce nearly spherical granulated particles and then coated. The raw medicament and the granulated particles are preferably in the size range of about 3 to 500 microns.

Details of a preferred process of rotogranulating and subsequent fluid-bed coating are provided in the examples section. Preferred methods are further described in: Jones, D. M. "Factors to Consider in Fluid-Bed Processing," *Pharmaceutical Technology*, Apr. 1985, Pg. 50–63; and Jager, K. F. et al., "Effect of Material Motion on Agglomeration in the Rotary Fluidized-Bed Granulator", *Drugs Made Germany*, Vol. XXV, Pg. 61–65 (1982). The entire disclosure of these articles are hereby incorporated herein by reference. Granulations comprising famotidine, PVP and lactose produced by rotogranulation are disclosed in co-pending U.S. patent application Ser. No. 07/859,593, filed Mar. 23, 1992, which is a continuation of application Ser. No. 575,465, filed Aug. 30, 1990, now abandoned, which is hereby incorporated herein by reference. Conventional top spray and wet granulation techniques may also be used in the present invention to form the granulated medicament.

Rotogranules have increased strength due to the compaction or densification of the granulation mixture as rotogranules are formed by rotation in the rotogranulator bed. This resistance to breakage is advantageous since broken particles are of a smaller size and are not readily coated in subsequent coating steps. Smaller sized particles without proper coating detract from the taste masking purpose of the coating by providing poor taste to the mixture as a whole. Further, smaller sized particles tend to agglomerate and interfere with subsequent fluid bed coating operations.

For some medicaments, including acetaminophen, granulation may not be a necessary preparatory step to produce desirable coated medicaments in accordance with the invention. The process and materials of the invention are applicable as coatings for a wide variety of medicaments which are preferably released in the gut or upper G-I tract and these include but are not limited to acetaminophen (APAP), ibuprofen, ibuprofen sodium, dexibuprofen lysinate, naproxen, naproxen sodium, and other similar NSAID's and their salts, psyllium, and the general class of antihistamines (e.g. chlorpheniramine, astemizole) gastrointestinal drugs (e.g. loperamide and famotidine) and decongestants (e.g. pseudoephedrine) as well as salts and combinations thereof. These raw medicaments are preferably in the particle size range of about 3 to about 500 microns.

In preferred embodiments of the compositions and processes of the invention, the medicament, in the raw or granulated form, is coated with a polymer blend of from about 5 to 95% MM/MAE and 5 to 95% of a cellulose ester, preferably CA, CAB, CTA or a combination thereof. The coated medicament, together with other ingredients such as flavoring agents, extenders, excipients, and the like, are compressed into tablet form.

Cellulose esters such as cellulose acetate and cellulose acetate butyrate, and cellulose triacetate are quite water insoluble but are soluble in organic solvents. They can provide good taste masking properties since they do not dissolve in the mouth and are tough enough to remain effectively intact during processing and normal chewing in the mouth. If used alone, however, a poorly soluble cellulose ester coating would not provide adequate ready release and bioavailability of the active ingredient after swallowing the chewed tablet. To provide the requisite ready release and bioavailability in the digestive tract and particularly in the acid medium of the stomach, MM/MAE is added to the polymer blend coating mixture.

Cellulose acetate, e.g., CA 398-10 or CA 320-S, or cellulose triacetate, e.g., CA 435-75S, available from FMC Corp., may be used in the blend. CA 398-10 polymer has an acetyl content of about 39.8 weight percent, a hydroxyl content of about 3.4 weight percent, a degree of substitution of 2.7 and a solution viscosity of about 38 poises or 10 seconds, as determined by ASTM Method D 1343 in the solution described as Formula A, ASTM Method D 871. The typical weight average molecular weight, according to the manufacturer, is 177,000 and the typical number average molecular weight is 58,500. CA 320-S polymer has an acetyl content of about 32.0 weight percent, a hydroxyl content of about 9.0 weight percent and a degree of substitution of 2.1. In a solution of 90:10 $CH_2Cl_2$:methanol, at 4% (w/w) concentration, the viscosity is 50 centipoise. The typical weight average molecular weight is 100,500 and the typical number average molecular weight is 63,500. CA 435-75S has an acetyl content of about 43.6 weight percent and a hydroxyl content of about 0.9 weight percent.

Cellulose acete butyrate, e.g., CAB 171-15S, CAB 381-2 and CAB 500-1 available from FMC Corp., may also be used in the blend. CAB 171-15S has a butyryl content of 17 weight percent, a hydroxyl content of 1.5 weight percent and a viscosity of 24 centipoises in a 4 weight percent solution of methylene chloride:methanol (90:10) one day after solution preparation at 25° C. CAB 381-2 has a butyryl content of 37 weight percent, an acetyl content of 13 weight percent and a hydroxyl content of 1.5 weight percent. CAB 500-1 has a butyryl content of 50 weight percent, an acetyl content of 5 weight percent and a hydroxyl content of 0.5 weight percent.

The preferred MM/MAE used in accordance with the present invention is identified by its tradename EUDRAGIT® E-100, available from Rohm Pharma. "E-100" signifies that the polymer EUDRAGIT E is a solid and MM/MAE is present in 100% in that solid, whereas, EUDRAGIT E 12.5 is a lacquer solution containing 12.5% MM/MAE. EUDRAGIT E brand acrylic resin is a copolymer based on dimethylaminoethyl methacrylates and neutral methacrylic acid esters with a mean molecular weight of 150,000, a viscosity of 3–12mPas at 20° C., a refractive index of $N^{20}_D$:1.380–1.385 and a relative density of $d^{20}_4$:0.810–0.820, as a 12.5% solution in acetone.

Further, other additives such as PVP or 2-vinyl pyridine (V)/styrene (S) copolymer may be added to the polymer blend coating. PVP is a polymer which is soluble in both water and organic solvents. The water solubility of PVP provides bioavailability of the coated active medicament in the gastrointestinal (GI) tract. When the coated granules are swallowed, the active medicament becomes bioavailable via permeation as the coating disintegrates. Permeation can occur through the intact coating, but is enhanced by the disintegration of the coating which becomes porous through dissolution of the water soluble PVP and/or MM/MAE in the stomach. PLASDONE® K-29/32 available from GAF Corporation is an example of a PVP polymer suitable for use in the polymer blend coating. The polymer weight ratio of V to S in the 2-vinyl pyridine (V)/styrene (S) copolymer is about 65/35 or 80/20.

The MM/MAE, cellulose ester and optionally PVP polymer blend has good mechanical flexibility which is advantageous in a product where the coating must withstand the forces of tablet compression and chewing in the mouth. Further, addition of taste neutral cellulose ester and/or PVP to poor tasting MM/MAE provides a useful taste mask coating. Use of MM/MAE alone would result in a poorly tasting chewable medicament. A high enough proportion of the coating of MM/MAE, cellulose ester and optionally PVP remains effectively intact on the medicament granules through the compression of the tablet and through normal chewing in the mouth to permit effective taste masking of unpleasant tasting medicaments. The term "effectively intact" means that the coating remains sufficiently integral to mask the taste or flavor of the medicament. This taste masking is effective to mask the unpleasant flavor of the medicament without requiring large and bulky amounts of overpowering flavoring agents.

MM/MAE, CA, CTA and CAB are not very soluble, if at all, in water, and are more conveniently applied from an organic solvent solution. Solubility of optional ingredient PVP in organic solvents permits ready mixing with MM/MAE and cellulose esters. MM/MAE, CA, CTA and/or CAB with or without PVP form clear compatible solutions in organic solvents, preferably acetone/methanol mixtures or acetone alone, which are suitable for pharmaceutical coating. The polymer blend of the invention provides the balance needed for good taste masking while being chewed in the mouth, along with either rapid or sustained bioavailability of the active medicament in the GI tract after swallowing.

The coated medicament may be made by coating the granulated or raw medicament with an organic solvent solution of the polymers in a fluidized bed coating operation. A wide variety of organic solvents may be used to prepare the organic solvent solution of the coating polymers. For instance, a more preferred solvent is acetone-methanol mixtures or acetone, but other solvent systems may also be used, including preferably methylene chloride-methanol (e.g. 9:1), ethanol, and isopropyl alcohol. Other solvents include methyl alcohol, ethyl alcohol, ethyl alcohol/water 6:4, isopropyl alcohol, n-butyl alcohol, propylene glycol, ethylene glycol, monobutyl ether, acetone, methyl ethyl ketone, cyclohexanone, methylene chloride, chloroform, carbon tetrachloride, trichloroethylene, tetrachloroethylene, ethyl acetate, n-butyl acetate, propylene glycol acetate, toluene, and white spirits 100°–140° C.

The polymers are dissolved in the solvent and the polymer solution is then coated onto the raw medicament or medicament granules or other active ingredient or combination of ingredients, using a fluidized bed coater. Air (which may be heated) passes through a bed of the medicament granules to fluidize them, and the solvent solution of the two polymers is sprayed onto the fluidized bed and thereby coats the rotogranules. The air passing through the bed dries the coated medicament, so that a dry coated particle is obtained. The coated particles are then used in combination with various excipients, flavors, and colors to make a chewable tablet.

The dried coating is present in an amount ("taste masking effective amount") sufficient to mask the otherwise disagreeable taste of the medicament while in the mouth of the user. The dried coating generally constitutes about 2–55%, preferably about 2–25% and most preferably about 8–16% of the total dry weight of the coated medicament, in the granulated form, or about 20–55%, preferably about 30–45%, of the total dry weight of the coated medicament, in the raw form. The exact proportions of coating to medicament desired for individual cases can be determined by routine experimentation. General considerations for determining coating amounts include physicochemical characteristics of the active i.e. solubility, pKa and the like, composition of the granule i.e. types of excipients and their physicochemical properties, CA, CTA, or CAB:MM/MAE ratio. Generally as CA, CTA, or CAB is increased the sustained release effect increases and the tastemasking increases. However, if the relative amount CA, CTA or CAB is increased too much the active may not be released entirely and the pH sensitivity of the blend may be lost. The particle size of the medicament, in the raw or rotogranular form, also has an effect on the coating amounts. The smaller particles generally require a higher coating level.

The amount of coating may be varied in light of the intended application and desired bulk of the products. Chewable tablets can be acceptable in larger sizes than swallowed tablets since chewing will reduce the size of the tablets in the mouth. Larger proportions of coating may be used to provide a sustained releasing or better tasting formulation.

When two or more medicaments are utilized in tablets of the present invention the coatings may be varied to provide a slower release of one medicament over another. This is especially advantageous for dosing a combination of medicaments that are more effectively released in different parts of the digestive tract or are better released separately in the digestive tract to avoid interference with each other or other incompatibility. Further, the same medicament may be subject to different coating compositions and amounts to provide for sustained release of some portion of the medicament and immediate release of another portion of the medicament to achieve an optimal dosing versus time profile. Obtaining such optimal dosing/time profiles depends upon the particular medicaments and medical needs required. The exact proportions of coating materials used, to achieve these profiles can be determined by routine experimentation.

As a general rule, the proportion of polymer in solution will be preferably from about 5 to 18 or 20, more preferably about 5 to 14, and most preferably about 10 weight percent, depending upon the process parameters. As a practical matter, a concentration of less than 5% polymer blend would unduly lengthen the coating process and a concentration of more than 18 to 20% would hamper spraying of the thickened solution.

Further, the coating of the invention provides a convenient means for providing a viable dosage form for combination medicaments which are incompatible before (e.g. during storage) or after administration.

An illustrative preferred procedure for coating the medicament in accordance with the invention is briefly described here and provided in more detail in the following examples section. The medicament, in the granulated or raw form, is preferably placed in a fluidized bed coater and is fluidized by a flow of air. When coating various medicaments, a product temperature of from about 20° C. to 40° C. preferably 25° C. to 35° C., is maintained. The rate of air flow is adjusted so as to fluidize the medicament particles. Such flow will vary depending on factors such as the specific equipment used, the size of the medicament charge, the size of the individual medicament particles, the apparent specific gravity of the medicament, and other factors that are known to those skilled in the art of fluidized bed coating. The air temperatures are monitored to provide an increase in temperature of the inlet air from 35° C. to 65° C. during the coating run. The outlet air is maintained at approximately 25° C. to 35° C. during the coating run. These temperatures may vary with different polymer blend ratios or with different actives.

After the medicament has been fluidized, the polymer solution is sprayed via bottom, top or tangential spray onto the fluidized bed. The air flow through the bed is continued until the amount of solvent remaining in the coating has been greatly reduced. The medicament particles are actually dry to the touch within a very short time after the coating solution has been sprayed onto the particles of the medicament; a matter of a few seconds in some cases. The total drying time required to ensure that the solvent content of the coating has been reduced to the level desired may take much longer, depending on the solvent used, temperature of the air, size of the batch, and the like. Routine experimentation will suffice to determine the appropriate air temperatures and total times required in the fluidized bed coaters in individual cases.

The invention will now be illustrated by examples. The examples are not intended to be limiting of the scope of the present invention but read in conjunction with the detailed and general description above, provide further understanding of the present invention and an outline of a process for preparing the medicament compositions and chewable medicament tablets of the invention.

EXAMPLES

The Examples below set forth the ingredients and proportions for typical laboratory scale preparations of coated medicaments. Unless otherwise stated, all ratios and percentages are by weight.

The coating methods used are disclosed for example in Jones, D. M. "Factors to Consider in Fluid-Bed Processing,, *Pharmaceutical Technology*, April 1985 and rotogranulating methods are taught by, for example, in Jager, K. F. et al., "Effect of Material motion on Agglomeration in the Rotary Fluidized-Bed Granulator", *Drugs Made in Germany*, Vol-XXV, Pp. 61–65 (1982) which have been incorporated herein by reference. The term "total coat" refers to the proportion of coating to uncoated medicament, in the raw or granulated form, in the coated medicament product, concentration of "polymer solution" to the proportion of polymer in the organic solvent solution, and "total batch" to the weight of medicament plus coating.

EXAMPLE I

Preparation of coated medicament, in the raw or rotogranulated form: A coating solution of polymers as identified below is prepared by adding the polymers to the organic solvents with stirring. The material to be coated is placed in a fluidized bed coater and is fluidized by the flow of air.

The temperature of the air may be a critical factor if high concentrations of EUDRAGIT E-100 are used and should be maintained between 25° C. and 40° C. If temperatures go below 25° C. degrees the medicament becomes too wet and can mass together. If the temperature goes above 40° C. degrees the EUDRAGIT can become tacky and cause massing of material. The rate of air flow is adjusted so as to fluidize the medicament. The coating material is then sprayed using a Wurster or rotogranulator insert. After the coating process is complete the coated granules are, if necessary, dried for a short period of time. Since organic solvents are used, they may be driven off rapidly, in a few seconds, with temperatures above 25° C. To be sure all organics are driven off to a safe level, the product may be dried for longer time periods. Routine experimentation will suffice to determine the appropriate air temperatures and total times required in the fluidized bed coaters in individual cases.

| | | |
|---|---|---|
| Total acetaminophen (raw form) charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 (39.8% acetyl content) | 15.0 | 0.073 |
| B EUDRAGIT E-100 (MM/MAE) | 50.0 | 0.244 |
| C PVP K29-32 (Avg. M.W. of about 40,000) | 35.0 | 0.171 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLES II–IX

The procedure of Example I is carried out using the following ingredients:

EXAMPLE II

| | | |
|---|---|---|
| Total acetaminophen (raw form) charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 85.0 | 0.415 |
| B EUDRAGIT E-100 | 15.0 | 0.073 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE III

| | | |
|---|---|---|
| Total acetaminophen (raw form) charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 60.0 | 0.293 |
| B EUDRAGIT E-100 | 40.0 | 0.195 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE IV

| | | |
|---|---|---|
| Total acetaminophen (raw form) charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 40.0 | 0.195 |
| B EUDRAGIT E-100 | 60.0 | 0.293 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE V

| | | |
|---|---|---|
| Total acetaminophen (raw form) charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 25.0 | 0.122 |
| B EUDRAGIT E-100 | 75.0 | 0.366 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE VI

| | | |
|---|---|---|
| Total acetaminophen (raw form) charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 15.0 | 0.073 |
| B EUDRAGIT E-100 | 85.0 | 0.415 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE VII

| | |
|---|---|
| Total ibuprofen rotogranule charge (kg): | 4.000 |
| % Solids in soln: | 10.000 |
| Total polymer (kg): | 0.444 |
| 10% Excess (kg): | 0.488 |
| Total coating soln (kg): | 4.880 |
| Total solvent wt. (kg): | 4.392 |

-continued

| POLYMER NAME | % POLYMER | POLYMER WT. (kg) |
|---|---|---|
| A CA 398-10 | 20.0 | 0.098 |
| B PVP K-29/32 | 40.0 | 0.195 |
| C EUDRAGIT E-100 | 40.0 | 0.195 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE VIII

| | | |
|---|---|---|
| Total loperamide rotogranule charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 20.0 | 0.098 |
| B PVP K-29/32 | 40.0 | 0.195 |
| C EUDRAGIT E-100 | 40.0 | 0.195 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE IX

| | | |
|---|---|---|
| Total famotidine rotogranule charge (kg): | | 4.000 |
| % Solids in soln: | | 10.000 |
| Total polymer (kg): | | 0.444 |
| 10% Excess (kg): | | 0.488 |
| Total coating soln (kg): | | 4.880 |
| Total solvent wt. (kg): | | 4.392 |
| POLYMER NAME | % POLYMER | POLYMER WT. (kg) |
| A CA 398-10 | 60.0 | 0.293 |
| B PVP K-29/32 | 10.0 | 0.049 |
| C EUDRAGIT E-100 | 30.0 | 0.146 |
| TOTAL | 100.0 | 0.488 |
| SOLVENT | % SOLVENT | SOLVENT WT. (kg) |
| A Methanol | 20.0 | 0.878 |
| B Acetone | 80.0 | 3.514 |
| TOTAL | 100.0 | 4.392 |

EXAMPLE X

The functions of several ingredients utilized in this Example X and some typical replacements for them are as follows:

Mannitol is a sweetener which can be replaced by dextrose, fructose, sorbitol, compressible sugar, xylitol, lactitol, and/or lactose;

Microcrystalline cellulose is used to improve tablet properties;

Aspartame is an artificial sweetener which can be replaced with others such as saccharin;

Magnesium stearate is a lubricant (to lubricate the dye walls and punches used during the tablet compression procedure). It can be replaced by talc, stearic acid, calcium stearate, zinc stearate, leucine, glycerides, sodium stearyl fumarate or the like; and artificial and natural flavor agents can be any conventional artificial and natural flavoring agents and flavor enhancers such as vanilla, grape, peppermint, orange, cherry, and/or spearmint flavors and conventional flavor enhancers or sweeteners.

PREPARATION OF CHEWABLE TABLETS

The ingredients displayed below were dry blended and compressed by standard procedures into round (disc shaped) chewable tablets, each weighing 395 mg. Each tablet contained 80 mg. of active acetaminophen. Raw acetaminophen was coated in accordance with the procedure of Example I with a polymer blend of 50% MM/MAE, 15% CA, and 35% PVP.

Preparation of Chewable Tablets: The following materials (excluding the coated APAP) are dry blended and then compressed into tablets.

| | |
|---|---|
| Mannitol | 1749.3 g |
| Microcrystalline Cellulose | 210.0 g |
| Aspartame | 35.0 g |
| Citric Acid Anhydrous | 14.7 g |
| Prosweet | 8.4 g |
| Flavor | 27.3 g |
| Magnesium Stearate | 27.3 g |
| APAP (coated) | 697.18 g[(1)] |

[(1)]Based on 19.7% coat for 7000 tablets at 395 mg/tablet.

EXAMPLE XI

Using the procedure of Example 1, raw ibuprofen (IBU) was coated, using acetone as the solvent and the following coating ingredients:

Sample A

| | | |
|---|---|---|
| Total ibuprofen charge (kg): | | 1.000 |
| % Solids in soln: | | 12.000 |
| Total polymer (kg): | | 0.818 |
| 10% Excess (kg): | | 0.900 |
| Total coating soln (kg): | | 7.500 |
| Total solvent wt. (kg): | | 6.600 |
| POLYMER NAME | % POLYMER | POLYMER WT. (kg) |
| A CA 398-10 (39.8% acetyl content) | 50.0 | 0.450 |
| B EUDRAGIT E-100 (MM/MAE) | 50.0 | 0.450 |
| Total | 100.0 | 0.900 |

Sample B

| | | |
|---|---|---|
| Total ibuprofen charge (kg): | | 1.000 |
| % Solids in soln: | | 12.000 |
| Total polymer (kg): | | 0.818 |
| 10% Excess (kg): | | 0.900 |
| Total coating soln (kg): | | 7.500 |
| Total solvent wt. (kg): | | 6.600 |
| POLYMER NAME | % POLYMER | POLYMER WT. (kg) |
| A CA 398-10 (39.8% acetyl content) | 60.0 | 0.540 |

-continued

| | | |
|---|---|---|
| B EUDRAGIT E-100 (MM/MAE) | 40.0 | 0.360 |
| Total | 100.0 | 0.900 |

Sample C

| | |
|---|---|
| Total ibuprofen charge (kg): | 1.000 |
| % Solids in soln: | 12.000 |
| Total polymer (kg): | 0.818 |
| 10% Excess (kg): | 0.900 |
| Total coating soln (kg): | 7.500 |
| Total solvent wt. (kg): | 6.600 |

| POLYMER NAME | % POLYMER | POLYMER WT. (kg) |
|---|---|---|
| A CA 398-10 (39.8% acetyl content) | 70.0 | 0.630 |
| B EUDRAGIT E-100 (MM/MAE) | 30.0 | 0.270 |
| Total | 100.0 | 0.900 |

PREPARATION OF IBUPROFEN CHEWABLE TABLETS

The ingredients displayed below were dry blended and compressed by standard procedures into round (disc shaped) chewable tablets each weighing 385 mg. Each tablet contained 50 mg of active ibuprofen (IBU). The coated ibuprofen samples prepared above were used in the tablets. Preparation of Chewable Tablets: The following materials are dry blended and then compressed into tablets.

| TABLET A | |
|---|---|
| Ingredient | mg/tab |
| Microcrystalline Cellulose | 30.00 |
| Stearic Acid | 3.00 |
| Aspartame | 6.00 |
| Flavor | 5.20 |
| Citric Acid Anhydrous | 3.00 |
| Prosweet | 1.50 |
| Cab-o-sil | 0.25 |
| Dyes/Colors | 0.90 |
| Mannitol | 237.69 |
| Coated IBU (Sample A) | 97.46 (1) |
| Total | 385.00 |

(1) Based on 48.7% coat

| TABLET B | |
|---|---|
| Ingredient | mg/tab |
| Microcrystalline Cellulose | 30.00 |
| Stearic Acid | 3.00 |
| Aspartame | 6.00 |
| Flavor | 5.20 |
| Citric Acid Anhydrous | 3.00 |
| Prosweet | 1.50 |
| Cab-o-sil | 0.25 |
| Dyes/Colors | 0.90 |
| Mannitol | 237.69 |
| Coated IBU (Sample B) | 97.67 (1) |
| Total | 385.00 |

(1) Based on 48.8% coat

| TABLET C | |
|---|---|
| Ingredient | mg/tab |
| Microcrystalline Cellulose | 30.00 |
| Stearic Acid | 3.00 |
| Aspartame | 6.00 |
| Flavor | 5.20 |
| Citric Acid Anhydrous | 3.00 |
| Prosweet | 1.50 |
| Cab-o-sil | 0.25 |
| Dyes/Colors | 0.90 |
| Mannitol | 235.55 |
| Coated IBU (Sample B) | 99.60 (1) |
| Total | 385.00 |

(1) Based on 49.8% coat

The release rate of ibuprofen from Tablets A, B and C was measured in accordance with USP Type II Dissolution Method. The dissolution media had a pH of 5.6. The results are as follows:

| Time (Min.) | Ibuprofen Released (Wt. %) Tablet | | |
|---|---|---|---|
| | A | B | C |
| 0 | 0 | 0 | 0 |
| 10 | 39.2 | 40.2 | 19.5 |
| 15 | 52.9 | 53.0 | 24.8 |
| 30 | 72.3 | 67.4 | 33.6 |
| 45 | 83.4 | 76.8 | 41.6 |
| 60 | 89.9 | 81.7 | 41.9 |

The above results demonstrate that the ibuprofen dissolution rate increases with the concentration of MM/MAE in the polymer blend forming the coating.

The scope of the present invention is not limited by the description, examples and suggested used herein and modifications can be made without departing from the spirit of the invention. For example, other components may be added to the tablets including additional actives, various flavorings, preservatives and other pharmaceutical excipients. The present invention may also be used to provide a chewable form for vitamins, minerals or other nutrients.

Application of the compositions and processes of the present invention for medical and pharmaceutical uses can be accomplished by any clinical, medical and pharmaceutical methods and techniques as are presently and prospectively known to those skilled in the art. Thus it is intended that the present invention cover the modifications and variations of this invention provided that they come within the scope of the appended claims and their equivalents.

What is claimed is:

1. A chewable medicament tablet comprising a medicament composition coated with a taste masking effective amount of a polymer blend consisting essentially of from about 5 to about 95 weight percent by total weight of the polymer blend of dimethylaminoethyl methacrylate and neutral methacrylic acid ester and from about 5 to about 95 percent by total weight of the polymer blend of a polymer selected from the group consisting of cellulose acetate, cellulose triacetate or a combination thereof.

2. The chewable tablet of claim 1 wherein the polymer blend coating comprises from about 2 to 55% by weight of the total weight of the coated medicament composition.

3. The chewable tablet of claim 1 wherein the polymer blend consists essentially of about 10 to about 90% of dimethylaminoethyl methacrylate and neutral methacrylic acid ester and about 10 to about 90% of cellulose acetate or cellulose triacetate, by weight of the total weight of the polymer blend.

4. The chewable tablet of claim 1 wherein the medicament composition to be coated is spherical in shape.

5. The chewable tablet of claim 2 wherein the medicament composition comprises a medicament selected from the group consisting of acetaminophen, ibuprofen, dexibuprofen lysinate, naproxen, naproxen sodium, psyllium, chlorpheniramine, astemizole, loperamide, famotidine, ranitidine, cimetidine, pseudoephedrine, salts thereof and combinations thereof.

6. The chewable tablet of claim 3 wherein the medicament is selected-from the group consisting of acetaminophen, ibuprofen, dexibuprofen lysinate, naproxen, naproxen sodium, psyllium, chlorpheniramine, astemizole, loperamide, famotidine, ranitidine, cimetidine, pseudoephedrine, salts thereof and combinations thereof.

7. The chewable tablet of claim 6 wherein the tablet additionally comprises pharmaceutically acceptable excipients.

8. A process of preparing a chewable medicament tablet comprising the steps of:

coating a medicament composition with a taste masking effective amount of polymer blend consisting essentially of about 5 to about 95 weight percent by total weight of the polymer blend of dimethylaminoethyl methacrylate and neutral methacrylic acid ester and about 5 to about 95 weight percent by total weight of the polymer blend of a polymer selected from the group consisting of cellulose acetate, cellulose triacetate and combinations thereof; and forming a chewable tablet by compressing the coated medicament composition in the presence of excipients.

9. The process of claim 8, further comprising the step of granulating the medicament to form said medicament composition.

10. The process of claim 8 wherein the polymer coating comprises from 2 to 55% by weight of total weight of the coated medicament composition.

11. A method for taste masking medicaments comprising coating a medicament composition with a taste masking effective amount of a polymer blend consisting essentially of from about 5 to about 95 weight percent by total weight of the polymer blend of dimethylaminoethyl methacrylate and neutral methacrylic acid ester and about 5 to about 95 weight percent by total weight of the polymer blend of a polymer selected from the group consisting of cellulose acetate, cellulose triacetate and combinations thereof.

12. The method of claim 11 wherein the medicament composition comprises a medicament selected from the group consisting of acetaminophen, ibuprofen, ibuprofen sodium, dexibuprofen lysinate, naproxen, naproxen sodium, psyllium chlorpheniramine, astemizole, loperamide, famotidine, ranitidine, cimetidine, pseudoephedrine salts thereof and combinations thereof.

* * * * *